United States Patent
Kebel et al.

(10) Patent No.: US 7,625,391 B2
(45) Date of Patent: Dec. 1, 2009

(54) ORTHOPAEDIC RATCHETING FORCEPS

(75) Inventors: Roland Kebel, Selzach (CH); Christoph Rusch, Biel (CH); Urs Brönimann, Biel (CH)

(73) Assignee: Stryker Trauma S.A. (CH)

( * ) Notice: Subject to any disclaimer, the term of this patent is extended or adjusted under 35 U.S.C. 154(b) by 624 days.

(21) Appl. No.: 10/532,180

(22) PCT Filed: Nov. 3, 2003

(86) PCT No.: PCT/CH03/00718

§ 371 (c)(1),
(2), (4) Date: Nov. 14, 2005

(87) PCT Pub. No.: WO2004/041099

PCT Pub. Date: May 21, 2004

(65) Prior Publication Data

US 2006/0149315 A1 Jul. 6, 2006

(30) Foreign Application Priority Data

Nov. 4, 2002 (EP) .................................. 02405938

(51) Int. Cl.
*A61B 17/00* (2006.01)
(52) U.S. Cl. ....................... 606/203; 606/208
(58) Field of Classification Search ......... 606/201–203, 606/205–211, 170–174, 151, 153, 157, 158; 600/490, 499
See application file for complete search history.

(56) References Cited

U.S. PATENT DOCUMENTS

| 4,538,485 A | * | 9/1985 | Saila ........................... 81/336 |
| 4,896,661 A | | 1/1990 | Bogert et al. |
| 5,176,702 A | | 1/1993 | Bales et al. |
| 5,373,866 A | | 12/1994 | Whalen, II |
| 5,674,244 A | * | 10/1997 | Mathys ........................ 606/208 |

FOREIGN PATENT DOCUMENTS

| DE | 242 254 C | 1/1912 |
| DE | 20 25 868 A | 12/1971 |
| DE | 28 49 009 A | 6/1979 |
| DE | 91 09 113.6 U | 2/1992 |
| DE | 93 14 581.0 U | 11/1993 |
| DE | 100 49 379 A | 4/2002 |
| WO | WO-89/06939 A1 | 8/1989 |

* cited by examiner

*Primary Examiner*—Kevin T Truong
(74) *Attorney, Agent, or Firm*—Lerner, David, Littenberg, Krumholz & Mentlik, LLP

(57) ABSTRACT

An orthopaedic ratcheting forceps, especially for fixation of fractures, comprises two handles, wherein a first catching element is mounted pivotally with one handle and wherein a complementary catching element is mounted in the other handle. The forceps can assume only two stable settings which can be switched with a single hand, one closed setting within which the jaws of the forceps can only be further closed and an open setting within which the handles of the forceps are freely movable so that the forceps can be opened as well as closed. In one handle a leaf spring is provided and biased between two mounting points which spring is mounted between abutting side walls within said handle. Furthermore a lever end connected with one of the catching elements engages the spring and through movement of the activation element the lever end and/or the spring is switchable between the closed setting and the open setting.

21 Claims, 6 Drawing Sheets

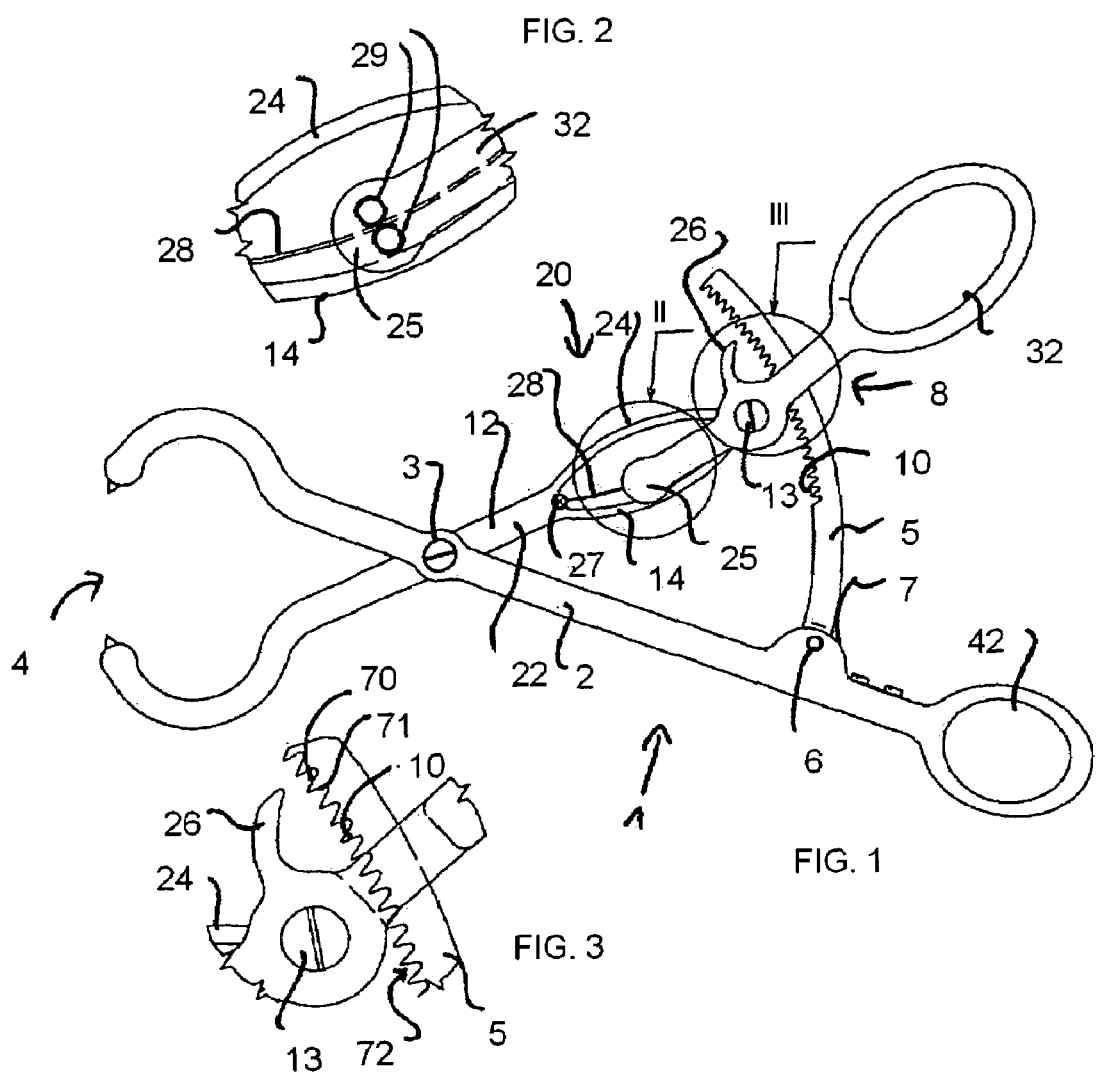

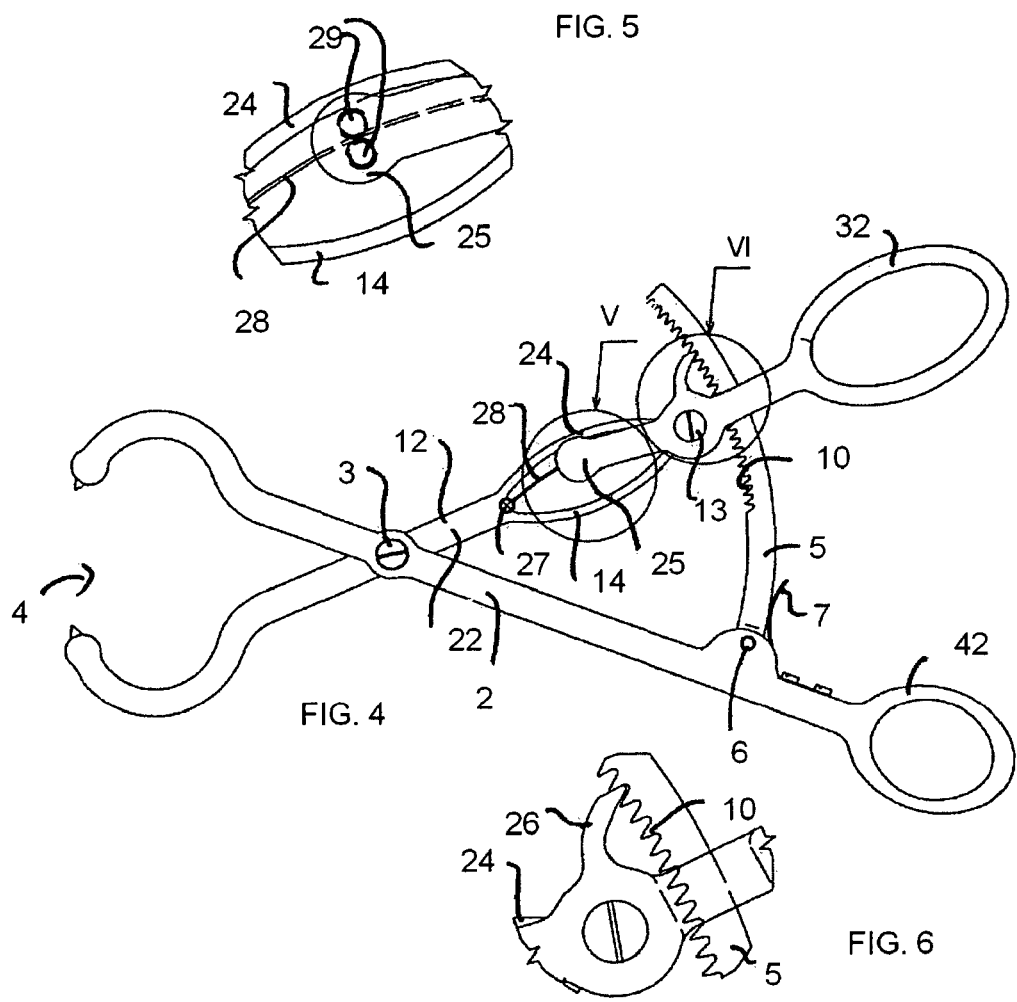

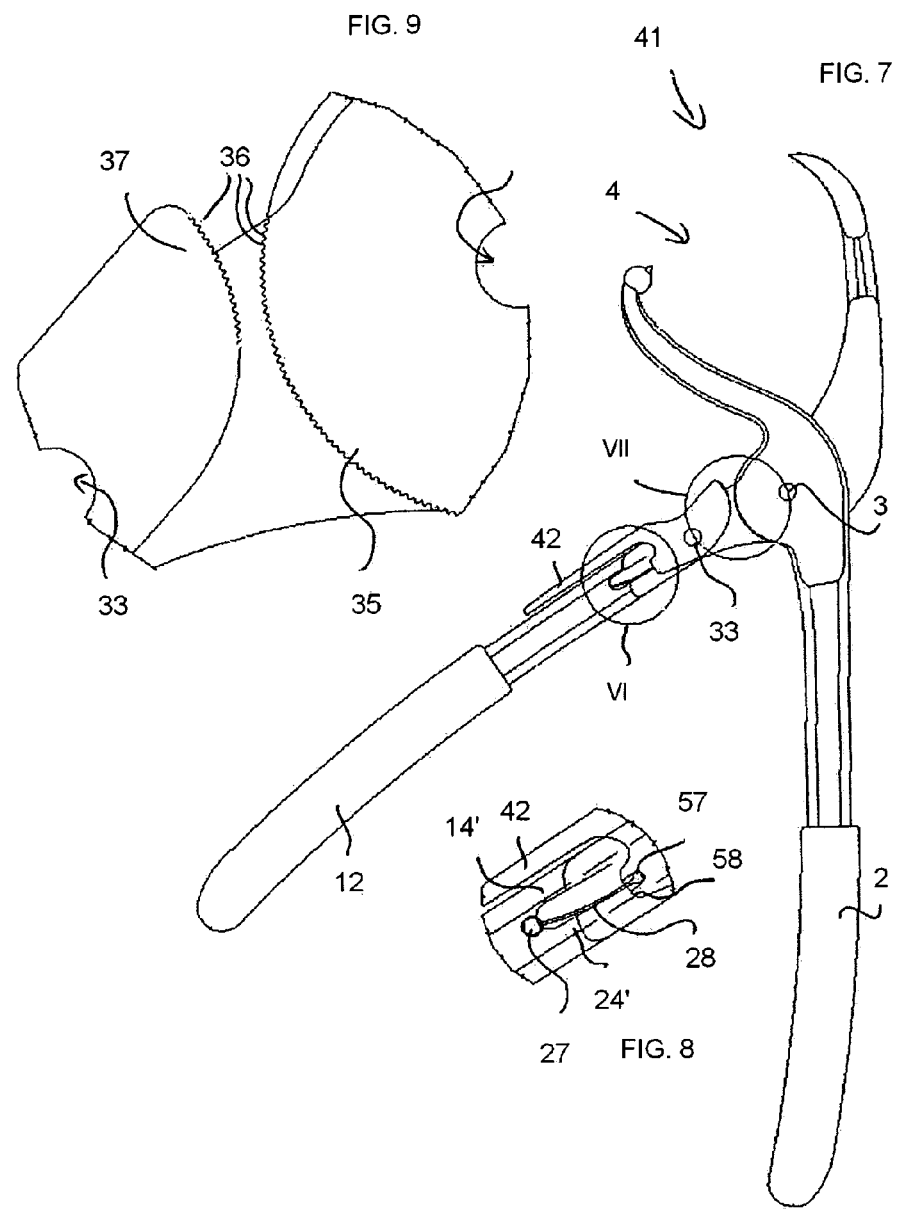

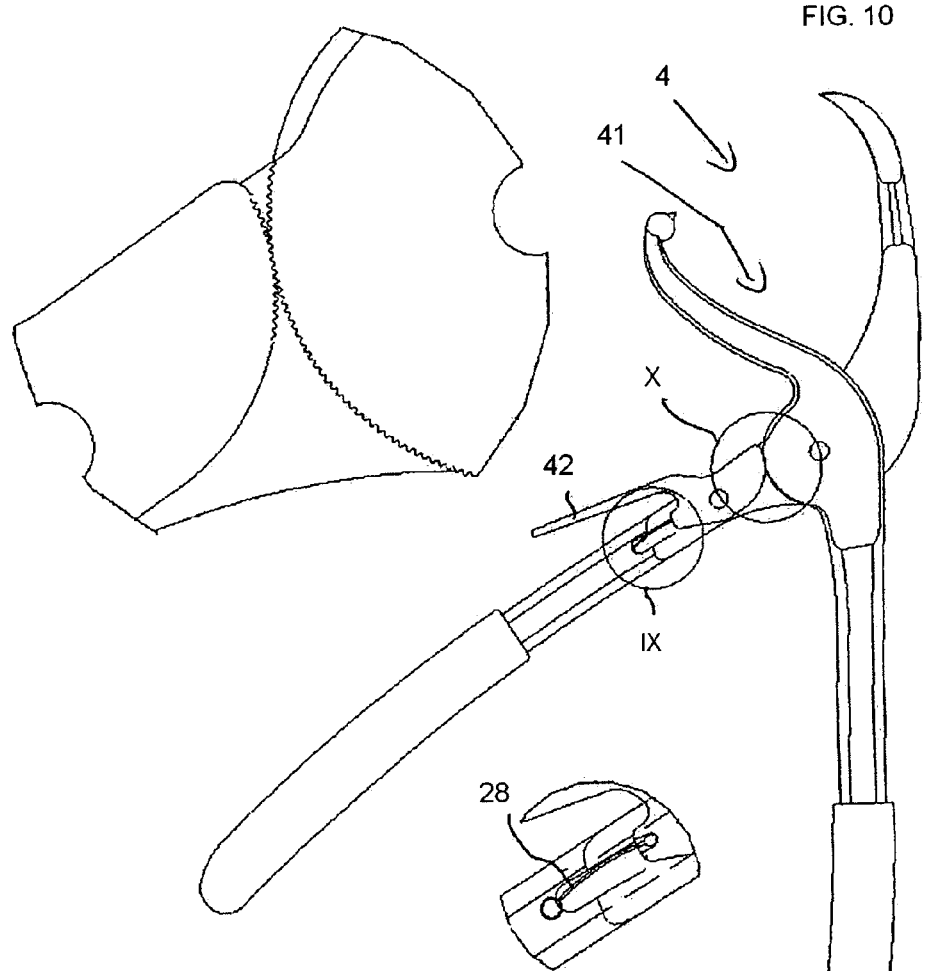

ORTHOPAEDIC RATCHETING FORCEPS

BACKGROUND OF THE INVENTION

The invention relates to an orthopaedic ratcheting forceps and specifically to a forceps used to manipulate and hold the bone for fixation of fractures.

The prior art shows a multitude of manipulating devices for use during orthopaedic surgery. An exemplary forceps according to the preamble of the main claim of this invention is shown in WO 89/06939 (U.S. Pat. No. 4,896,661). Beside the fact of the possibility to interchange tips of the forceps as shown in said application, another important practical point for the surgeon is the possibility to change the attack point of the forceps, i.e., to have a reversible ratchet mechanism. The advantage of the ratchet according to said PCT application resides in the fact, as shown in FIGS. 9, 8 and 9, that through switching a lever through three switching positions the forceps can move freely (FIG. 9, neutral position) or in either direction (FIG. 10 or FIG. 11, respectively). Although this approach facilitates the work of the surgeon, it has been found not to be entirely satisfactory. The mechanism is difficult to manipulate with only one hand.

Another known forceps is disclosed in U.S. Pat. No. 5,674,244. The pliers according to this document have the advantage that almost all of the ratcheting structure is within the handles and do not extend beyond the outer form of the instrument. There is provided a spring to exert the counterforce to open the pliers, when the release button is pushed. The advantage of reduced dimensions of the forceps goes with the practical disadvantage in activating the locking device of the pliers between the handles.

SUMMARY OF THE INVENTION

In view of this prior art the object of the invention is to provide an orthopaedic ratcheting forceps for a surgeon giving him better control for the locking device and at the same time strengthen the security of the pliers.

BRIEF DESCRIPTION OF THE DRAWINGS

Further objects and advantages are achieved through the features of the subclaims and exemplary embodiments of the invention are disclosed in the following description in which:

FIG. 1 is a view in side elevation of a forceps according to a first embodiment of the invention with the locking device in an open setting;

FIG. 2 is an enlarged view of the lever portion within circle II in FIG. 1;

FIG. 3 is an enlarged view of the locking portion within circle Ill in FIG. 1;

FIG. 4 is a view in side elevation of the forceps according to FIG. 1 with the locking device in a closed setting;

FIG. 5 is an enlarged view of the lever portion within circle V in FIG. 4;

FIG. 6 is an enlarged view of the locking portion within circle VI in FIG. 4;

FIG. 7 is a view in side elevation of a forceps according to a second embodiment of the invention with the locking device in an open setting;

FIG. 8 is an enlarged view of the lever portion within circle VI in FIG. 7;

FIG. 9 is an enlarged view of the locking portion within circle VII in FIG. 7;

FIG. 10 is a view in side elevation of the forceps according to FIG. 5 with the locking device in a closed setting;

FIG. 11 is an enlarged view of the lever portion within circle IX in FIG. 10;

FIG. 12 is an enlarged view of the locking portion within circle X in FIG. 10;

DETAILED DESCRIPTION OF THE DRAWINGS

Figure 13:
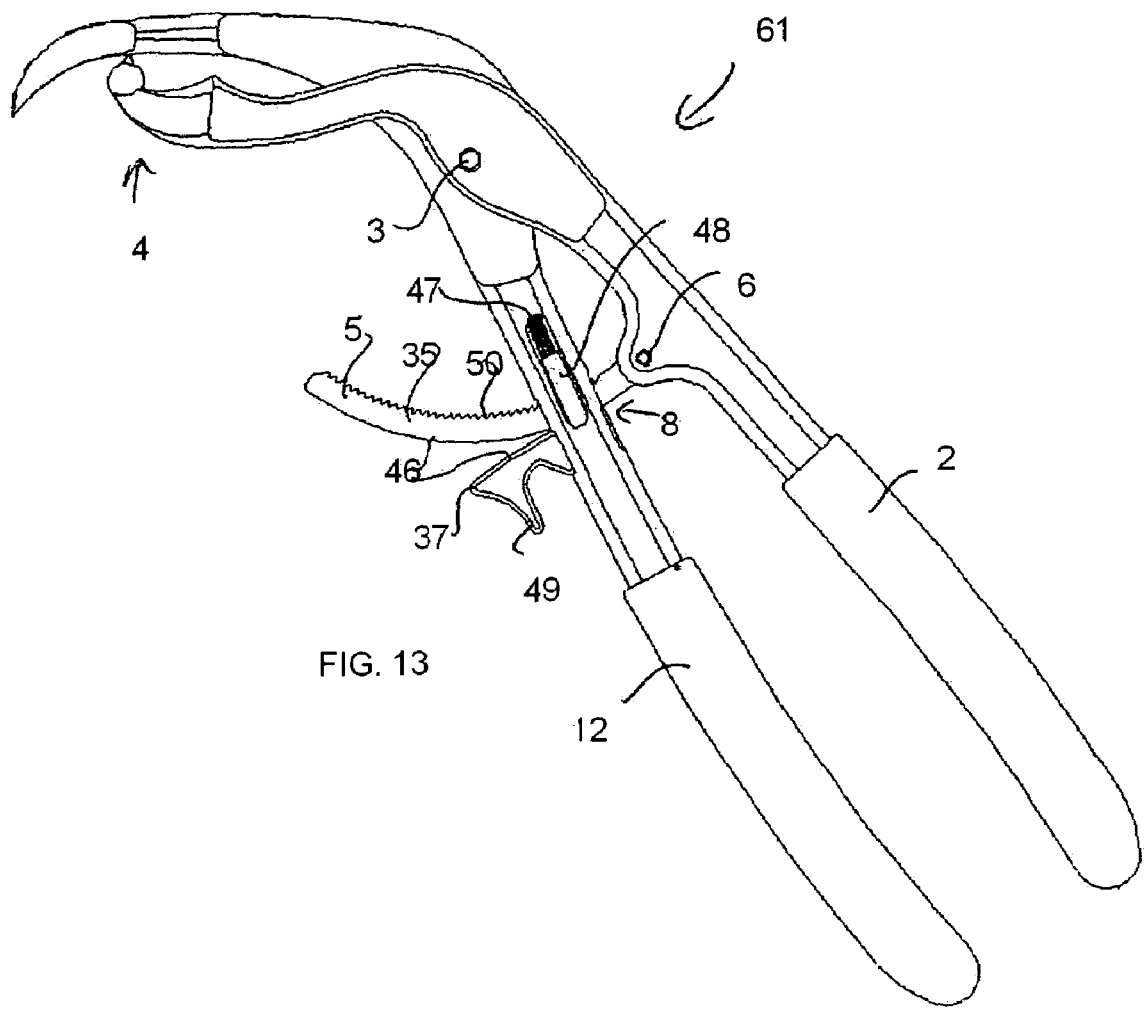
FIG. 13 is a view in side elevation of a forceps according to a third embodiment of the invention with the locking device in an open setting.

FIG. 1 shows a view in side elevation of a forceps 1 according to a first embodiment of the invention with the locking device in an open setting, i.e., in a setting in which the handles 2 and 12 are freely movable about a pivot point 3. The forceps 1 has jaws 4 comprising sharp points provided to enter into bone material and/or surgical plates and bone material. It is clear that other configurations may be chosen, e.g., that the jaws comprise internal teeth.

On the inner side of handle 2, a shaped rod 5 is pivotally mounted by means of a pin 6. A leaf spring 7 pushes the rod 5 from the outer side of the handle 2 into the direction or towards the pivot point 3. In a more simple embodiment the spring 7 may be omitted, especially if the guiding bore 8 (not shown) within the second handle 12 is sufficiently narrow. The rod 5 comprises a number of catching elements or ratchet teeth 10. These may comprise grooves in a transversal direction to the longitudinal axis of the slightly curved rod 5. The rod 5 is preferably slightly curved, having a radius of curvature equivalent to the distance from the pivot point 3. The grooves or notches (catching elements 10) are provided on the inside of the rod 5, i.e., directed towards the pivot point 3.

As mentioned above, within the second handle a guiding bore 8 is located with e.g., rectangular dimensions to accommodate the rectangular rod 5. If the rod 5 is more or less round then the guiding bore 8 may be cylindrical, or a rounded slit etc.

The second handle 12 comprises a second pivot point 13 in the neighborhood of the bore 8, dividing the handle 12 in one fingerhole part 32 and in one jaw part 22, hinged together at said second pivot point 13. This allows for a locking structure 20 to be mounted between the first and second pivot points 3 and 13, respectively, of the handle 12. The jaw part 22 of the second handle 12, nearby the pivot point 13, splits of in two arms 14 and 24 between which the end 25 of the fingerhole part 32 is located. The two arms 14 and 24 join together in one end point which may advantageously be in the vicinity of the pivot point 13. Said end 25 can be moved between the inner sides of the arms 14 and 24. In the position of FIG. 1 where end 25 is positioned toward arm 14 a nose 26 integrally, mounted on fingerhole handle part 32, is free and does not engage the catching elements 10 of rod 5.

Between two end points (27 and here pivot point 13) of the arms 14 and 24, respectively, is provided a leaf spring 28. Leaf spring 28 engages the end 25 of fingerhole part 32 and is part of the lever and locking mechanism of the ratchet. In the preferred embodiment, spring 25 is made of spring steel and supplies sufficient force to maintain the nose 26 into engagement with the teeth of arm 5 when deflected towards arm 24.

FIG. 2 is an enlarged view of the lever portion within circle II in FIG. 1. Same features in all drawings always have the same reference numerals. Spring 28 is mounted with the transversal direction of the leaf perpendicular to the drawing plane and therefore parallel to the axes of the pivot points 3 and 13. Therefore two noses 29 provided parallel one to another and encompassing the leaf spring 28 are mounted on the end 25 and extending into the space between the arms 14 and 24 provide guiding means for the spring 28. Since the spring 28 is biased, i.e., longer than the length of a direct line between the end points 27 and 13 of the arms 14 and 24, the end 25 can only take two stable positions, one open setting according to FIG. 1 (deflected towards arm 14) and one closed setting according to FIG. 3 (deflected towards arm 24). The noses 29 may be small bolts or cylinders with enough play between them to allow the movement of the spring 28, the surface of the bolts 29 on the opposite side to the position of the spring 28 can be directly used to abut against the arm 14 or arm 24, respectively.

FIG. 3 is an enlarged view of the locker portion within circle III in FIG. 1. The teeth 10 comprise two different slopes 70, 71. Slope 71, which is the slope oriented towards fixation point 6, is more or less perpendicular to the current longitudinal axis of rod S. The other slope 70 is inclined in direction of fixation point 6 with an angle between preferably 30 and 60 degrees in comparison to the direction of slope 71.

FIG. 4 shows a view in side elevation of the forceps 1 according to FIG. 1 with the locking device in a closed setting, i.e., in a setting in which the handles 2 and 12 are only movable about the pivot point 3 in a direction closing the jaws 4 of the forceps 1. FIG. 5 is an enlarged view of the lever portion within circle V in FIG. 4. As can be seen in comparison of the two settings of the forceps in FIGS. 1 and 4, the handles 2 and 12 are freely movable (i.e., they can be opened). There can be an additional spring, not shown in FIGS. 1 and 4, between handles 2 and 12 in the vicinity of pivot point 3, urging the handles 2 and 12 apart. Otherwise (without said spring) the forceps may be opened by the surgeon as he would do with scissors. Upon pushing the handle 12 and especially the fingerhole part 32 towards the other 5 fingerhole part 42, a moment is exerted upon the spring 28 through the lever provided through second pivot point 13 and the lever length to the end 25. This moment pushes the spring 28 out of the stable open setting as shown in FIG. 1 towards the second stable setting as shown in FIG. 4, the closed setting. Through the movement of the fingerhole part 32 relative to the jaws part 22 of the handle 21 the nose 26 engages one of the catching elements 10 of rod 5. Therefore upon releasing the fingerhole parts 32 and 42, a counter pressure upon the jaws 4 of forceps 1 will not open the handles 2 and 12 because the forceps 1 is in a stable closed setting. However, the surgeon has the possibility to further close the fingerhole parts 32 and 42. To ensure the possibility of this movement the catching elements 10 of rod 5 and the nose 26 are formed asymmetrically, ensuring that the nose 26 can glide from one catching element 10 to the next one which is nearer to the pivot point 6 while forbidding the inverse movement.

The surgeon can also very easily release the grip of the forceps through pushing the fingerhole 32 apart from the fingerhole 42, disengaging the nose 26 from the catching elements 10, when the setting according to FIG. 1 is reached. This means that he controls the opening and closing of the forceps 1 through simple manipulation and relative movement of the fingerhole parts 32 and 42. There is no need for a separate switch, button or release mechanism.

FIG. 6 is an enlarged view of the locker portion within circle VI in FIG. 4. Two teeth 10 with their two neighbouring different slopes 70, 71 are in engagement with the nose 26, which preferably has a complementary form to the groove 72 which is formed by the slopes of adjacent teeth 10, therefore blocking the movement of the rod 5 in one direction and allowing said movement 40 in the other direction.

The embodiment according to FIGS. 1 to 4 is not the only possibility to achieve such advantageous handling of a forceps. FIG. 7 is a view in side elevation of a forceps 41 according to a second embodiment of the invention with the locking device in an open setting. All features within the embodiment of FIG. 7 having similar features within the embodiment according to FIG. 1 have the same reference numerals. FIG. 8 show an enlarged view of the lever portion within circle VI in FIG. 7 and FIG. 9 is an enlarged view of the locking portion within circle VII in FIG. 7. Within this embodiment a release button 42 is provided in parallel to one handle 12. The principle of the forceps 41 is as follows. A cylindrical locking element 35 is provided on or integral to handle 2. This locking element 35 comprises at least a rough surface, preferably comprising small transversal grooves 36. A complementary locking element 37 is provided with the release button 42 being realised as a lever arm extending in parallel to handle 12. The complementary locking element 37 comprises grooves or teeth 36 which are arranged along a curve with a changing curvature, i.e., the radius of curvature becomes greater between the position of the element 37 which is named the open setting in relationship to the position which is named the closed setting.

The open setting of FIG. 7 is achieved through a biased spring 28 extending between one end point 27 inside a lengthy slit between two webs 14' and 24' and another endpoint 57 near the pivoting point 33. In order to achieve the closed setting as shown in FIG. 10 showing a view in side elevation of the forceps 41 according to FIG. 7 with the locking device in an closed setting, and as the detailed view of FIG. 11 an enlarged view of the lever portion within circle IX in FIG. 10, and FIG. 12, an enlarged view of the locking portion within circle X in FIG. 10. Through a pivoting of the lever 42 away from the handle 12 the two complementary surfaces 35 and 37 mutually engage and through the special form of the surface 37 the forceps 41 can not open anymore since the spring 28 now urges the lever 42 in the second stable setting, the closed setting.

Figure 14:
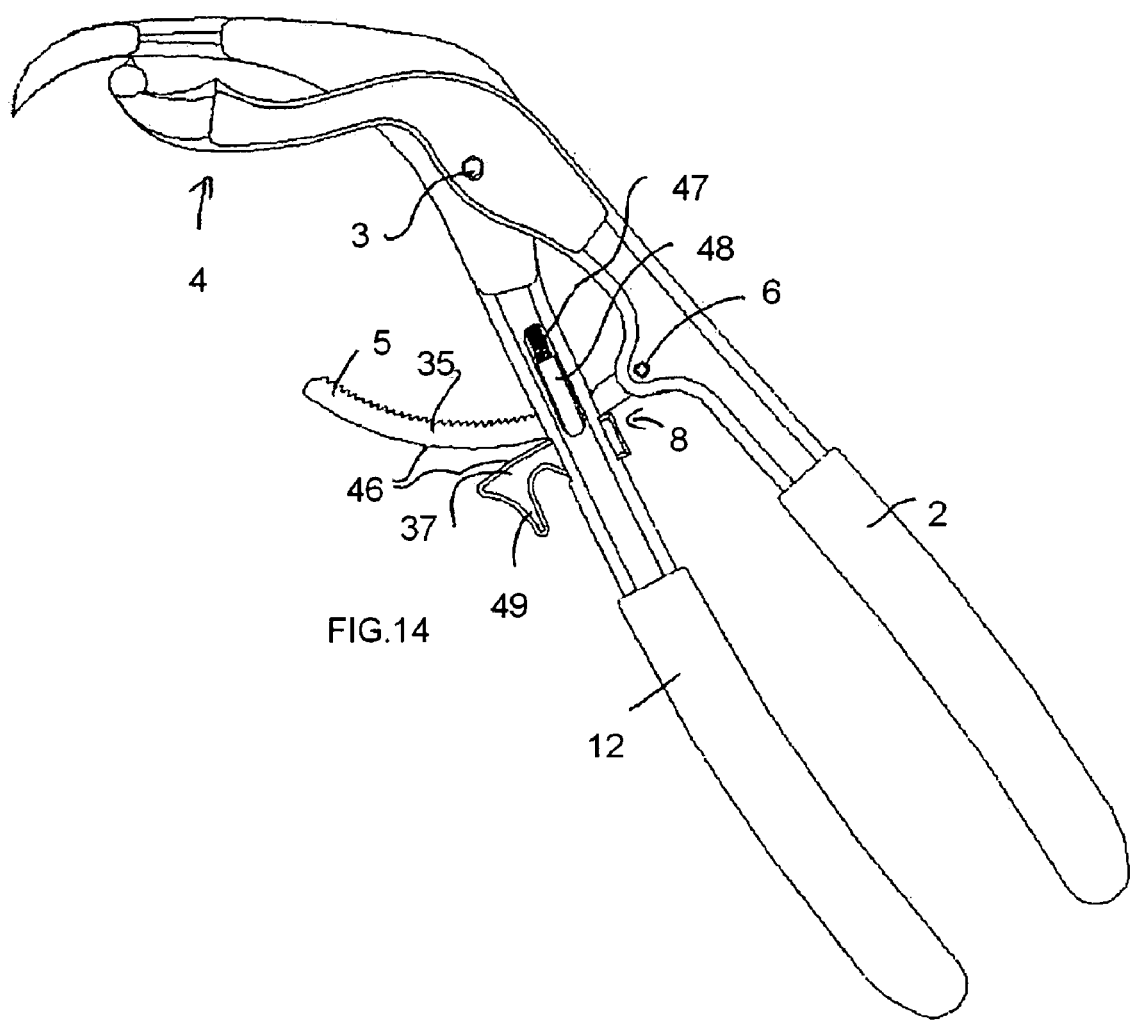
FIG. 14 is a view in side elevation of the forceps according to FIG. 13 with the locking device in a closed setting.

Finally FIG. 13 shows a view in side elevation of a forceps 61 according to a third embodiment of the invention with the locking device in an open setting, and FIG. 14 shows a view in side elevation of the forceps 61 according to FIG. 13 with the locking device in a closed setting.

On the inner side of handle 2, a shaped rod 5 is swivel-mounted by means of a pin 6. The guiding bore 8 within the second handle 12 accepts the rod 5. The rod 5 comprises a number of catching elements 50. These may comprise grooves in a transversal direction to the longitudinal axis of the slightly curved rod 5. The rod 5 is preferably slightly curved, having a radius of curvature equivalent to the distance from the pivot point 3. The grooves or notches (catching elements 10) are provided on the inside of the rod 5, i.e., directed towards the pivot point 3. Within the second handle 12 is located a bolt 48, which is pushed in direction of the rod 5 through a spring 47 which may be a disk spring and which is placed in the second handle 12 between the bolt 48 and the pivot point 3 acts to move surface 46 of rod 5 towards surface 46 of an element 37. In the open setting shown in FIG. 13 the surfaces 46 of element 37 and rod 5 are not in engagement, whereas in FIG. 14 the element 37 is pushed inside the forceps 61 therefore bringing the surfaces 46 in contact one to another achieving the same function as within the second embodiment, i.e., preventing the jaws 4 from opening but allowing closure. The arrangement according to FIGS. 13 and 12 allows a further compression, just gliding the surfaces 46 one against another. However, there is no backwards travel, which can only be achieved through pushing the element 37 towards the outside through pushing the nose 49 in either direction (from FIG. 13 to FIG. 14 and vice versa).

In all embodiments the release or fixation element is directly usable when gripping the forceps, either through manipulation within the fingerholes 32 as in the first embodiment, or through a release lever 42 in parallel to the handle as in the second embodiment, or through a bolt 48 releasing element, provided in parallel to the second handle as in the third embodiment.

One of the advantages of the embodiment according to FIG. 1 is the possibility to switch from the open to the closed setting through movement of the handles. There is no additional button or lever to be manipulated. Therefore the surgeon can switch the device into the closed setting, engage the device within the body to be gripped, close the jaws 4 further, while within this closed setting the surgeon is sure that one position of the jaws reached they will not open any more. If now the grip has to be loosened, the surgeon can switch from the closed setting to the open setting without leaving the gripping holes of the handles. Then he opens the jaws and continues to work on the same body to be gripped or another without loosing time.

The second advantage of the embodiment shown in FIG. 7 to 10 is the reduced space requirement and the button 49 is still easily reached since mounted in a natural position for the hand. This result can be reached through the definition of the surfaces 36 within the elements 35 and 37, respectively. In the figures one element has a cylindrical curvature while the other has a changing radius of curvature. In the open setting (freely movable jaws 4) the two elements are in a small distance one from another when the distance is measured on the straight line between the two axes. When the button 42 is moved to the closed setting, the element 37 is rotated around the axis 33. Therefore the distance changes and eventually becomes zero. The surfaces 36 are engaging one another. When the surgeon now would try to open the jaws, i.e., move the second handle 2 away from the first handle 12, the two surfaces would rotate around the axes 33 and 3, respectively. But this rotation would diminish further the distance between said surfaces since one of the elements has a growing radius of curvature in this direction of rotation resulting in a blocking state. The further closing of the jaws through movement of the handles would move the elements in a direction where at least one element has a diminishing radius of curvature thus allowing this movement.

In order to ensure the best engagement of the surfaces they are provided with microgrooves or grooves in a direction perpendicular to the drawing sheets.

The invention claimed is:

1. A forceps comprising:
    a first member having a clamping portion at a first end and a gripping portion at a second end;
    a second member pivotally connected to said first member at a first pivot point, said second member having a clamping portion at a first end and a gripping portion at a second end, said first and second gripping portions adapted to be gripped by the thumb and fingers of a hand;
    a leaf spring mounted on the first members, the leaf spring having first and second ends, the first end mounted on the first member, the leaf spring spaced along a length of the first member, the leaf spring having a length greater than the length between the first and second ends along the first member so that the leaf spring can lie on either side of a straight line connecting the first and second ends thereof;
    a locking element mounted on said first member for engaging a complimentary locking element on said second member, said locking element on the first member having an element engaging the leaf spring for moving the leaf spring from a first side of the line to a second side of the line; and
    an actuator mounted on said first member for moving said locking element between a first locked position and a second unlocked position, the leaf spring biasing the locking element toward the first locked position when on the first side of the line and biasing the locking element toward the second unlocked position when on the second side of the line, said actuator adapted to be moved by said thumb or fingers of said hand while said gripping portions of said first and second members are gripped.

2. The forceps according to claim 1, wherein said leaf spring is mounted between side walls within said first member clamping portion.

3. The forceps according to claim 2, wherein said first member clamping portion and gripping portion are hinged together at a pivoting point, wherein said pivoting point is the second end of the spring and wherein said spring is confined between two convex, side walls of a clamping portion and a prolongation of a gripping portion of the first member forms the element which engages the leaf spring.

4. The forceps according to claim 3, wherein said locking element is a rod mounted pivotally on the second member, the rod extending through an opening within the gripping portion of the second member and having grooves on the side directed towards the gripping portions of the forceps and wherein the grooves of the rod can be engaged through the complementary locking element formed as a nose extending from said gripping portion of the first member.

5. The forceps according to claim 4, wherein said rod is prebiased in direction of the jaws of the forceps through the leaf spring pushing the rod in the direction of the grooves on the side directed towards the gripping elements.

6. The forceps according to claim 1, wherein the locking elements on the first and second members are curved elements wherein at least one locking element has a changing radius of curvature, in order to provide, in the closed setting —a blocking device upon contact of the surfaces of the catching elements prohibits further movement in the direction of opening the forceps.

7. The forceps as set forth in claim 1 wherein said gripping portion of said first member is a fingerhole portion pivotally coupled to said clamping portion of said first member and said actuator is actuated by movement of said fingerhole portion with respect to said clamping portion.

8. The forceps as set forth in claim 1 wherein said actuator is operatively coupled to said first member and has a finger engaging portion located adjacent a surface of said first member gripping portion remote from said second member gripping portion.

9. An orthopedic ratcheting forceps comprising:
    a first handle having a clamping portion at a first end and a gripping portion at a second end;
    a second handle pivotally connected to said first handle at a first pivot point, said second handle having a clamping portion at a first end and a gripping portion at a second end, said first and second gripping portions are adapted to be gripped by the thumb and fingers of a hand;
    a first catching element pivotally mounted with said first or second handle,
    a second catching element being complimentary to the first catching element and mounted with the other handle of the first or second handle, said first and said second catching element can assume only two stable settings which can be switched with said hand, one closed setting within the clamping portions can only be further closed and an open setting within which the handles are freely moveable, so that the forceps can be opened as well as closed;

a spring member arranged in said first handle or said second handle, wherein said spring member is biased between a first mounting point and a second mounting point;

a lever end which is connected with one of the catching elements engages the spring member;

an actuator which is in connection with said lever end for moving said lever end between the closed setting and the open setting;

wherein said second mounting point is the point of engagement of the lever end which can be switched between two side walls within said first handle and the first catching element and the complementary catching element are curved elements wherein at least one catching element has a changing radius of curvature to provide a blocking element when the forceps is in its closed setting upon contact of the surfaces of the catching elements against further movement in the direction of openings the forceps.

10. The forceps according to claim 9, wherein the actuator is the first handle which is pivotable.

11. The forceps according to claim 9, wherein the spring member is a leaf spring mounted within the first handle or wherein the spring member is a part of said first handle having a memory effect allowing for the two settings.

12. The forceps according to claim 11, wherein said spring member is mounted between facing side walls within said first handle.

13. The forceps according to claim 12, wherein said first handle comprises two portions hinged together at a pivoting point, wherein said pivoting point is the second mounting point of the spring and wherein said spring is confined between two, especially convex, side walls of the clamping portion of the two portions and the prolongation of the fingerhole portion of the two portions forms the lever end and engages the leaf spring.

14. The forceps according to claim 13, wherein said first catching element is a rod mounted pivotally on the second handle, the rod extending through an opening within the fingerhole portion and having grooves on the side directed towards the jaws of the forceps and wherein the grooves of the rod can be engaged through the complementary catching element formed as a nose extending from said fingerhole portion.

15. The forceps according to claim 14, wherein said rod is prebiased in direction of the clamping elements of the forceps through a spring pushing the rod in the direction of the grooves on the side directed towards the jaws.

16. The forceps according to claim 9, wherein said first catching element is a rod mounted pivotally on the second handle, the rod extending through an opening within the handle and having grooves on the side directed towards the clamping elements of the forceps and wherein the grooves of the rod can be engaged through the spring.

17. The forceps according to claim 9, wherein the complementary catching element is part of the activation element comprising the complementary catching elements which can be pushed inside said opening within the handle to disengage the spring from the rod.

18. The forceps according to claim 9, wherein said gripping portion of said first member is a fingerhole portion pivotally coupled to said clamping portion of said first member and said actuator is actuated by movement of said fingerhole portion with respect to said clamping portion.

19. The forceps according to claim 9, wherein said actuator is operatively coupled to said first member and has a finger engaging portion located adjacent a surface of said first member gripping portion remote from said second member gripping portion.

20. An orthopedic ratcheting forceps, comprising first and second handles, each handle having a jaw at one end thereof, wherein a first catching element is pivotally mounted with the first handle, wherein a complementary catching element is mounted on the second handle, wherein the catching elements can assume a closed and an open stable setting which can be switched with a single hand, the closed setting where the jaws of the forceps can only be further closed and the open setting wherein the handles of the forceps are freely movable, so that the forceps can be opened as well as closed, wherein a spring means is provided in the first handle, the spring means is biased between first and second mounting points, a lever end connected with one of the catching element engages the spring means and through movement of an activation element the lever end is switchable between the closed setting and the open setting, wherein the second mounting point is the point of engagement of the lever end which can be switched between two side walls formed with the first handle, and the first catching element and the complementary catching element are curved elements wherein at least one catching element has a changing radius of curvature, in order to provide, in the closed setting, a blocking device upon contact of the surfaces of the catching element against further movement in the direction of opening the forceps.

21. The forceps according to claim 20, wherein the spring means is a leaf spring mounted within the first handle having a memory effect allowing for the open and closed settings.

* * * * *

UNITED STATES PATENT AND TRADEMARK OFFICE
CERTIFICATE OF CORRECTION

PATENT NO. : 7,625,391 B2  Page 1 of 1
APPLICATION NO. : 10/532180
DATED : December 1, 2009
INVENTOR(S) : Kebel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1052 days.

Signed and Sealed this

Twenty-sixth Day of October, 2010

David J. Kappos
*Director of the United States Patent and Trademark Office*